United States Patent
DeBono et al.

(10) Patent No.: US 6,924,477 B2
(45) Date of Patent: Aug. 2, 2005

(54) METHOD AND SYSTEM FOR ESTABLISHING THE CLEANLINESS OF A DEVICE

(75) Inventors: Reno DeBono, Annandale, NJ (US); John J. Carroll, Madison, NJ (US); Robert Sandor, South Orange, NJ (US)

(73) Assignee: Smiths Detection Inc., Warren, NJ (US)

( * ) Notice: Subject to any disclaimer, the term of this patent is extended or adjusted under 35 U.S.C. 154(b) by 0 days.

(21) Appl. No.: 10/402,525

(22) Filed: Mar. 28, 2003

(65) Prior Publication Data

US 2004/0188604 A1 Sep. 30, 2004

(51) Int. Cl.$^7$ .............................................. B01D 59/44
(52) U.S. Cl. ...................... 250/282; 250/286; 250/287; 250/288
(58) Field of Search ................................ 250/282, 287, 250/286, 288, 281

(56) References Cited

U.S. PATENT DOCUMENTS

| | | | |
|---|---|---|---|
| 4,490,678 A | * 12/1984 | Kuisl et al. | 324/438 |
| 4,567,366 A | 1/1986 | Shinohara | |
| 4,806,765 A | * 2/1989 | Heinen | 250/389 |
| 4,943,929 A | * 7/1990 | Simonoff | 700/266 |
| 5,046,018 A | * 9/1991 | Flewelling et al. | 702/24 |
| 5,200,614 A | 4/1993 | Jenkins | |
| 5,281,816 A | 1/1994 | Jacobson et al. | |
| 5,300,773 A | * 4/1994 | Davies | 250/286 |
| 5,455,417 A | 10/1995 | Sacristan | |
| 5,587,581 A | 12/1996 | Stroosnyder | |
| 6,061,141 A | 5/2000 | Goldenberg et al. | |
| 6,385,558 B1 | 5/2002 | Schlemm | |
| 6,459,079 B1 | * 10/2002 | Machlinski et al. | 250/286 |
| 6,479,815 B1 | 11/2002 | Goebel et al. | |
| 6,495,824 B1 | 12/2002 | Atkinson | |
| 6,627,878 B1 | * 9/2003 | Machlinski et al. | 250/287 |

OTHER PUBLICATIONS

PCT International Search Report dated Nov. 8, 2004; 5 pgs.

* cited by examiner

*Primary Examiner*—John R. Lee
*Assistant Examiner*—Johnnie L Smith, II
(74) *Attorney, Agent, or Firm*—Foley & Lardner LLP

(57) ABSTRACT

A system and method for establishing the cleanliness of a device by performing a test is described. The system includes an ion mobility spectrometer to measure target signal strengths, and to measure $n_2 \geq 1$ test signal strengths of a device sample. The system also includes a statistics module to obtain a value of a statistical confidence-level parameter that is associated with a particular confidence level, and a pass range module to obtain a pass range of signal strengths from the value of the statistical confidence-level parameter and the $n_1$ target signal strengths. The system also includes an averaging module to obtain an average test signal strength from the $n_2$ test signal strengths, and a results module to determine that the device passes the test, indicating that the device is significantly clean to within the particular confidence level, if the average test signal strength lies in the pass range.

33 Claims, 2 Drawing Sheets

METHOD AND SYSTEM FOR ESTABLISHING THE CLEANLINESS OF A DEVICE

FIELD OF THE INVENTION

The invention relates to quantitative analysis using ion mobility spectrometry.

BACKGROUND OF THE INVENTION

It is often imperative that the cleanliness of a device, such as manufacturing equipment in the food or pharmaceutical industries, be established to meet safety regulations or guidelines. Contaminants in samples must be measured to determine if they are present below safe levels.

Most of the pharmaceutical industry currently uses high performance liquid chromatography (HPLC) to evaluate samples collected from production machines. Highly trained technicians in an analytical laboratory prepare the mobile phase and diluents and set up the HPLC instrument. Each sample collected is then prepared and, typically, through the use of an autoloader, injected and processed consecutively without operator intervention. As cleaning and sample preparation normally occupy a full working day, analysts load the instrument at the end of a one day then, in the following morning, perform any necessary calculations and enter the sample results in a database. Production usually resumes in the middle of that day, resulting in a loss of at least one and a half days.

SUMMARY OF THE INVENTION

The present invention uses ion mobility spectrometry to establish the cleanliness of a device. Ion mobility spectrometry refers to the principles, practice and instrumentation of characterizing chemical substances based on their gas phase ion mobilities as determined by measuring drift velocities as ions move, under the influence of an electric field, through a gas at ambient pressure. Typical pharmaceutical compounds are thermally desorbed to vaporize the sample. The vaporized sample is then introduced into the ion mobility spectrometer via a carrier gas stream before being selectively ionized. An electronic gate then opens periodically to admit a finite pulse of product ions into the drift tube. The ions migrate downfield and strike a collector electrode, producing a current. The ion current is amplified and displayed as an ion mobility spectrum or plasmagram, showing ion current versus time.

The method of the present invention uses ion mobility spectrometry to establish the cleanliness of a device. Because ion mobility depends on the size and shape of a molecule, the ion mobility can be used as a signature of a contaminant being tested. The method can be up to two orders of magnitude faster and can be much cheaper than HPLC. Moreover, the method does not require highly trained personnel to administer the test.

In particular, a system for establishing the cleanliness of a device by performing a pass/fail test is described herein. The system includes an ion mobility spectrometer to measure $n_1 \geq 1$ target signal strengths with the ion mobility spectrometer, and to measure $n_2 \geq 1$ test signal strengths of a device sample. The system further includes a statistics module to obtain a value of a statistical confidence-level parameter that is associated with a particular confidence level, and a pass range module to obtain a pass range of signal strengths from the value of the statistical confidence-level parameter and the $n_1$ target signal strengths. The system further includes an averaging module to obtain an average test signal strength from the $n_2$ test signal strengths, and a results module to determine that the device passes the test, indicating that the device is significantly clean to within the particular confidence level, if the average test signal strength lies in the pass range.

Also described herein is a method for establishing the cleanliness of a device based on a test that employs an ion mobility spectrometer (IMS), the method includes measuring $n_1 \geq 1$ target signal strengths with the IMS, and measuring $n_2 \geq 1$ test signal strengths of a device sample with the IMS. The method further includes obtaining a value of a statistical confidence-level parameter that is associated with a particular confidence level, and utilizing the value of the statistical confidence-level parameter and the $n_1$ target signal strengths to obtain a pass range of signal strengths. The method also includes calculating an average test signal strength from the $n_2$ test signal strengths, and determining that the device passes the test, indicating that the device is significantly clean to within the particular confidence level, if the average test signal strength lies in the pass range.

BRIEF DESCRIPTION OF THE DRAWINGS

For a better understanding of the present invention and to show more clearly how it may be carried into effect, reference will now be made, by way of example, to the accompanying drawings, in which.

DETAILED DESCRIPTION OF THE INVENTION

The cleanliness of devices, such as manufacturing equipment in the food or pharmaceutical industries, often has to be established to meet safety regulations or guidelines. The system and method described herein can be used to accurately and relatively cheaply establish that the amount of contaminant present does not exceed an acceptable level with a ceratin confidence.

Figure 1:
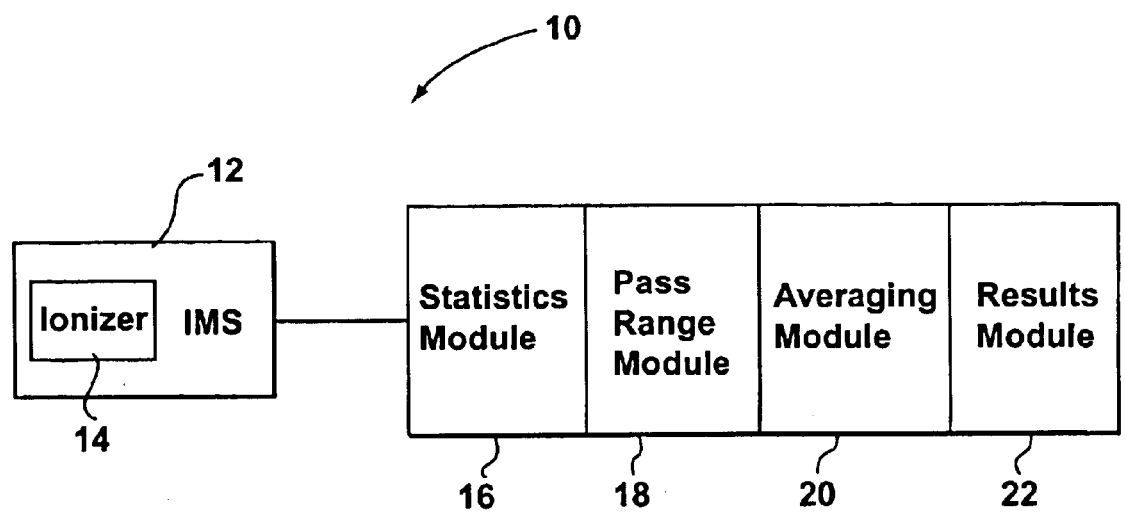
FIG. 1 shows a system for establishing the cleanliness of a device by performing a pass/fail test a system, in accordance with the principles of the present invention.

FIG. 1 shows a system 10 for establishing the cleanliness of a device by performing a pass/fail test. The system 10 includes an ion mobility spectrometer (IMS) 12 having an ionizer 14. The system 10 also includes a statistics module 16, a pass range module 18, an averaging module 20 and a results module 22.

The IMS 12 is used to measure $n_1 \geq 1$ target signal strengths and $n_2 \geq 1$ test signal strengths. The $n_2$ test signal strengths are measured by swabbing the device to obtain a device sample, which is then ionized and analyzed with the IMS 12, as described in more detail below.

To measure the $n_1$ target signal strengths, a target sample having a known target concentration of a contaminant is provided. The target sample is ionized with the ionizer 14 before subjecting the ionized sample to ion mobility spectrometry. In particular, a target signal strength of the sample is measured with the IMS 12. These steps of ionizing and measuring are repeated to obtain all $n_1$ target signal strengths.

The statistics module 16 includes hardware and/or software to obtain a value of a statistical confidence-level parameter that is associated with a particular confidence level, for a given $n_1$ and $n_2$. The statistics module 16 can include hardware such as a mouse, keyboard and computer display to input a particular confidence level. The statistics module 16 includes software and hardware to calculate the value of the statistical confidence-level parameter associated with the confidence level provided. For example, if a particular confidence level is input as a percentage, the statistics module 16 can calculate the associated Student's t parameter, as known to those of ordinary skill. The Student's t parameter helps to determine whether two distributions have the same mean. As applied to the instant invention, the Student's t parameter helps establish whether a difference between a first mean associated with the target signal strengths and a second mean associated with the test signal strengths is significant or due to chance. Alternatively, the Student's t parameter can be input directly via the statistics module 16.

The pass range module 18 includes hardware and/or software to obtain a pass range of signal strengths from the value of the statistical confidence-level parameter, the $n_1$ target signal strengths and the $n_2$ test signal strengths. In particular, the pass range module can include hardware such as a mouse, keyboard and computer display to input the $n_1$ target signal strengths and the $n_2$ test signal strengths. Alternatively, these can be input automatically, without human intervention, after the IMS 12 measures the target and test signal strengths. As described in more detail below, if the average test signal strength $\bar{y}$, which is computed by the averaging module 20 from the $n_2$ test signal strengths, falls within the pass range, the device is significantly clean to within the particular confidence level.

The results module 22 includes software and/or hardware that determines that the device passes the test, indicating that the device is significantly clean to within the particular confidence level, if the average test signal strength lies in the pass range. The results module 22 can include a display, which can produce an image or sound, indicating a pass or fail of the test for cleanliness.

Figure 2:
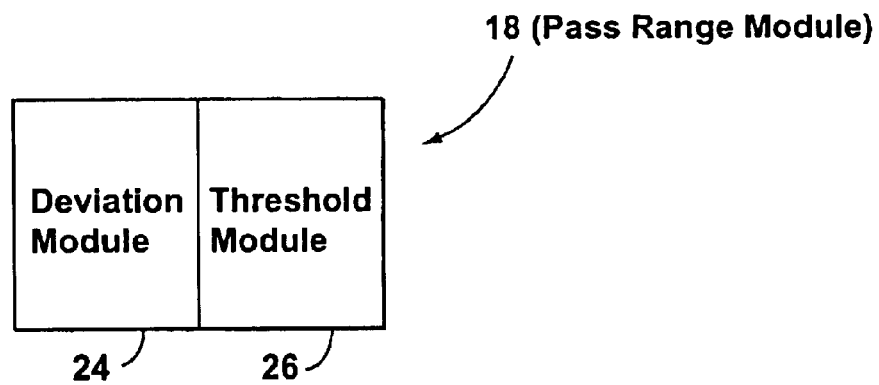
FIG. 2 shows the pass range module of FIG. 1.

FIG. 2 shows the pass range module 18 of FIG. 1. The pass range module 18 includes a deviation module 24 and a threshold module 26.

The deviation module 24 calculates a pooled standard deviation s to obtain the pass range. The pooled standard deviation, s, is given by $$s = \left[ \frac{\sum_{i=1}^{n_1}(x_i - \bar{x})^2 + \sum_{j=1}^{n_2}(y_j - \bar{y})^2}{n_1 + n_2 - 2} \right]^{1/2}$$

with $$\bar{x} = \frac{1}{n_1} \sum_{i=1}^{n_1} x_i$$

and $$\bar{y} = \frac{1}{n_2} \sum_{j=1}^{n_2} y_j,$$

where $\{x_1, \ldots, x_{n1}\}$ are the $n_1$ target signal strengths and $\{y_1, \ldots, y_{n2}\}$ are the $n_2$ test signal strengths.

The threshold module 26 calculates a threshold strength, $z_t$, given by $$z_t = \bar{x} - ts \sqrt{\frac{n_1 + n_2}{n_1 n_2}}. \tag{1}$$

The pass range is then given by $[0, z_t]$. Thus, if $y \in [0, z_t]$, then the device is significantly clean to within the particular confidence level, with respect to the particular contaminant contained in the target sample. On the other hand, the results module 22 determines that the device does not pass the test, indicating that the device is not significantly clean to within the particular confidence level, if the average test signal strength lies in a fail range given by the complement of the pass range, namely $(z_t, \infty)$.

The significance associated with the value of t is a number between zero and one, and is the probability that $|t|$ could be this large or larger just by chance, for distributions having equal means.

In one embodiment of the present invention, the results module 22 can further divide the fail range into two ranges, a first range $(z_t, \bar{x}]$, and a second range $(\bar{x}, \infty)$. If the average test signal strength $\bar{x}$ lies in the first range, then the results module 22 determines that the device is clean, but not significantly clean, and if the average test signal strength lies in the second range, then the results module 22 determines that the device is not clean.

Figure 3:
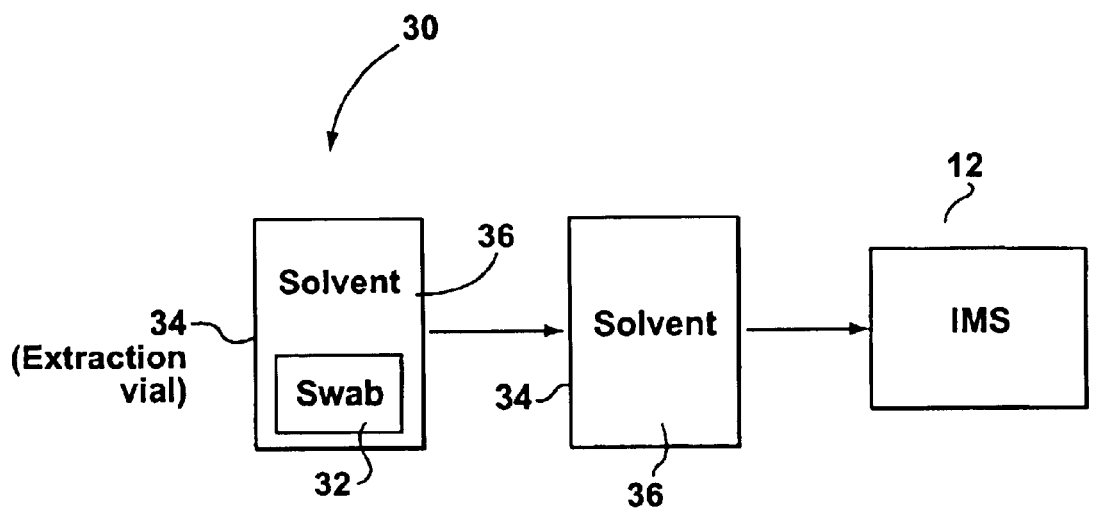
FIG. 3 shows apparatus of the system of FIG. 1 used for measuring test signal strengths.

In FIG. 3, apparatus 30 of the system 10 used for measuring the $n_2 \geq 1$ test signal strengths is shown. The apparatus 30 includes a swab 32 for swabbing the device and an extraction vial 34 having solvent 36 for extracting possible contaminants in the swab 32. The swab 32 can include cotton, polyester and nylon. Generally, a swab material is chosen that leaves no particulate material behind and does not interfere with the subsequent IMS analysis. The swab is taken from a fixed surface area of the device. The swab 32 is immersed in vial with a fixed volume of solvent 36, which can be water, acetone, methanol, ethanol or isopropanol, for example. The vial 34 can be sonicated or shaken, for example, to help the extraction. The swab 32 can be extracted multiple times and extracts combined and diluted to a fixed volume. The swab is then removed and the liquid phase is then filtered to remove particulate material before the solution is inserted into the IMS 12 so that the results module 22 can provide results of the test.

Figure 4:
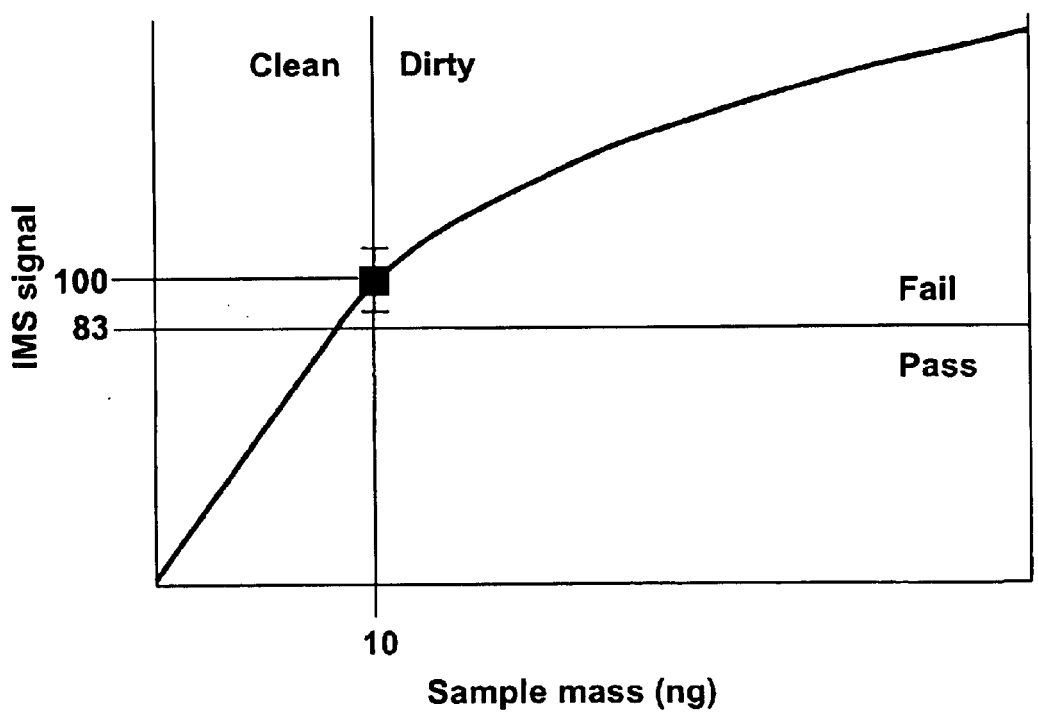
FIG. 4 shows a mass response curve of a particular contaminant.

Referring to FIG. 4, a mass response curve of a particular contaminant is shown that corresponds to (average) signal strength versus amount of contaminant (in nanograms). To obtain such a curve, the ion mobility of the contaminant is found. The ion mobility corresponds to a drift time, as known to those of ordinary skill. Signal strength readings from the detector of the IMS 12 can be made at the contaminant's drift time for varying amounts of contaminant. The resultant curve in FIG. 4 is monotonically increasing because the greater the amount of contaminant present, the greater the number of contaminant ions that reach the detector at the drift time (and hence the stronger the signal strength).

To swab with an appropriate amount of solvent 36, a target mass is selected, which is associated with the average target signal strength $\bar{x}$ above which the device is determined to be not clean. The target mass is that of the contaminant being tested that could be present in the solution inserted into the IMS 12. To select the target mass, which provides a compromise between the higher response per unit mass obtained with small masses and the smaller relative standard deviation obtained with larger masses, the limit of linearity of the curve in FIG. 4 is selected because the linear region has the highest sensitivity and generally provides the lowest relative standard deviation. Once the target mass is selected, which in the exemplary curve shown in FIG. 4 is ten nanograms, the amount of solvent 36 that is used to extract can be computed as follows.

The target mass and associated average target signal strength are found from the curve. In the schematic curve in FIG. 4, $\bar{x}=100$. Other factors to consider are the sample volume used to deliver the sample mass to IMS 12 (typically 1–10 microlitres), the target concentration (determined using target mass and sample volume), and target cleaning level on IMS 12 (typically 100–1000 ng/cm2). A worst case swabbing scenario is assumed, which is typically 60–90% recovery by swabbing.

The above factors are used to ensure that a swab at the action level is diluted to the target concentration. For example, if the target mass is 10 ng, the sample volume is 1 $\mu$L, the target cleaning action level is 200 ng/cm$^2$, the area to be swabbed is 100 cm$^2$ and the swabbing recovery is 80%, then the target concentration is 1 $\mu$g/mL and the action level on the swab is 16 $\mu$g. Thus, the volume to extract the swab should be 16 mL per swab.

Generally, the volume to extract the swab is $$V_{ex} = \frac{1}{1000} FDCA \frac{V_{ts}}{m_{ts}}$$

where $V_{ex}$ is the volume the swab is extracted into (in mL)
F is the recovery factor for swabbing the surface
D is the dilution factor required if the initial extract is very concentrated
C is the target surface concentration of the action-level surface (in ng/cm$^2$)
A is the area to be swabbed (in cm$^2$)
$V_{ts}$ is the target sample volume to be analyzed (in $\mu$L)
$m_{ts}$ is the target sample mass to be analyzed (in ng)

Thus, for the preceding example, F=0.8, D=1 (no dilution), C=200 ng/cm$^2$, A=100 cm$^2$, $V_{ts}$=1.0 $\mu$L, and $m_{ts}$=1 ng then the sample swab is extracted into 16 mL of solvent in order to properly dilute the sample.

With the target concentration in hand, the IMS 12 measures the signal strengths of several samples at the target concentration and calculates the mean $\bar{x}$. Swabs can then be taken of the device and test samples prepared with the correct amount of solution, as indicated above. If the mean test signal strength $\bar{y}$ lies in the pass range, then $\bar{y}$ is significantly smaller than $\bar{x}$, indicating a pass of the cleanliness test.

Referring to FIG. 4 by way of example, if ten analyses are run on target samples and the mean target signal strength is 100 digital units (du) with a standard deviation of 5 du, then, with the help of Equation (1), it can be determined that any solution producing a test signal strength of less than $z_t$=83 du for one measurement (i.e., $n_2$=1) is clean with at least 99.5% confidence. Because the time required to make a measurement with the IMS 12 is short, it is sensible to perform extra target measurements because they provide better predictions for the standard deviation, increase the limit threshold and, therefore, lower the chances of a false positive.

In most cases, the swab tests as 'clean' when first measured. In some instances, the swab response is well above the threshold, indicating the need for further cleaning. In rare cases, the swab response is slightly above the threshold. The IMS 12 generates results so quickly that in this situation it is advisable to analyze a few more aliquots of the sample before deciding to reclean. As stated above, the swab can be declared clean if the mean of replicate samples lies in the pass range. The pass/fail threshold is higher when replicate samples are analyzed because of the nature of the t-test. Several can precautions can be taken to protect against false negatives. The first is to verify the consistency of swab recovery. The second is to check the instrument response across the range of interest to validate the system response. The third is to evaluate the effect of potential interferences (excipients, for example) that may be present because, occasionally, the analyte signal may be suppressed by the presence of particular compounds, particularly detergents or excipients.

There are various ways of acquiring a sample from a device to be tested. As described above, one method is to swab a prescribed area, then extract the contaminant from the swab with solvent. A second method is to rinse a prescribed area of the device with solvent to prepare a sample for testing.

Experimental Section

The experimental details of a cleanliness test performed on a device are described in this section. An IonScan-LS (Smiths Detection, Warren, N.J., USA) IMS 12 was used. In a typical analysis, a substrate containing the sample of interest is placed on the desorber of the IMS, which is maintained at a fixed programmed temperature of 290° C. A carrier gas, air, transports thermally volatilized sample material into an ionization reaction region. Volatilized compounds are selectively ionized by the ionizer 14 having a $^{63}$Ni β-source and a controlled chemical ionization environment to produce molecular ions or ion clusters. The ions are then gated into the drift chamber of the IMS 12, at atmospheric pressure, where they are accelerated under an applied electric field toward a collector electrode. Identification of compounds is based on the calculation of their characteristic reduced ion mobility $K_0$ (cm$^2$/Vsec) values. $K_0$ is determined using the following equation:

$$K_0 \text{ observed} = K_0 \text{ internal calibrant} \times (\tau_{cal}/\tau_{obs})$$

where $\tau_{cal}$ is the drift time of the internal calibrant and $\tau_{obs}$ is that of the observed peak. The $K_0$ of the internal calibrant is a known value and the drift times of the calibrant and observed peak are experimentally measured values. In the external calibration procedure, the internal calibrant $K_0$ value to be used in this equation is set so the $K_0$ observed for the external (primary) calibrant has the value $K_0$=1.1600 (cocaine).

It should be understood that other carrier gasses, such as argon or nitrogen, can also be used. Likewise, other desorber temperatures, greater or less than 290° C., may be appropriate.

The polarity of the electric field applied to the drift region is either positive or negative, allowing for the analysis of positive or negative ions. Ions of the correct charge are accelerated from the reaction region towards the drift region. Each scan of the IMS spectrum starts when the gating grid opens briefly to admit a burst of ions into the drift tube, and ends just before the gating grid opens again. This interval is the 'scan period.' The data from several scans are co-added together to improve the signal-to-noise ratio and is called a 'segment.' A series of segments with characteristic ion peak patterns for the sample are obtained and can be displayed either as a series of individual segments versus desorption time in seconds (a 3-D plasmagram) or as an average of all segments obtained during the analysis (a 2-D plasmagram).

A test product and excipients, provided by GlaxoSmithKline™, were used as supplied. Pesticide-grade acetone was used to prepare the test product samples and the excipients were prepared in water or ethanol. Teflon substrate (0.45 micron porosity) was obtained from Osmonics™ (Minnetonka, Minn., USA).

A 1 µL aliquot of the sample was deposited on the Teflon substrate using a 1.0 µL syringe (SGE™, Melbourne, Australia) and allowed to evaporate for 15 s prior to analysis.

Eight standards containing 1 ng of the test product were analyzed to determine the pass/fail threshold. Forty-eight test solutions, ranging from 0.25–10 ng, were then analyzed. The goal was to verify that the limit test would identify samples containing less than 1.5 ng of the test product as clean and those containing at least 1.5 ng as not clean.

The target level data of the target samples can be summarized as follows: mass=1.5 ng, $n_1$=8, $\bar{x}$=398 du, s=10 du (RSD=2.6%), t=5.408 for 99.95% confidence, and $z_t$=339 du. The pass/fail threshold calculated from these eight data points is 339 du; hence, if one analysis of a test sample gives a signal strength of less than 339 du, then, with at least 99.95% confidence, it contains less than the action level amount of the active pharmaceutical ingredient (API).

Regarding the test sample data, twenty-four clean samples (containing less than 1.5 ng of the API) were analyzed. In 23 of these cases, the sample passed the cleanliness test. There was, however, one false positive. For the 24 "dirty" test samples, there were no false negatives. All dirty samples tested as such. In the case of the one false positive, the prescribed course of action would be to analyze two additional aliquots of that sample and to apply the limit test to the mean of the three results. The mean would be compared with a revised threshold, which is based on more measurements and is therefore higher. As a worst case example, the three highest responses for 1 ng (329,330 and 344 du) give a mean signal strength of 334 du, which is less than the revised threshold of 365 du for three test samples. The test sample would therefore be declared clean.

As part of method development and validation, potential interference effects caused by excipients were investigated. Three excipients were studied: magnesium stearate, hydroxypropyl methylcellulose (HPMC), and lactose. To test for interference, ten samples of the test product were run in the presence of 1000 ng of all three excipients simultaneously. Samples (1000 ng) of each excipient in solution were then analyzed. Only HPMC were detected. The maximum amplitude of the test product peak at $K_0$=0.9688 was used for comparison. The data show that there was no suppression of the test Product signal from a hundred-fold excess of the three excipients.

The much shorter analysis time for both method development and routine analysis encourages the large reduction in production downtime that can be achieved by switching from HPLC to IMS for cleaning verification.

It should be understood that various modifications and adaptations could be made to the embodiments described and illustrated herein, without departing from the present invention, the scope of which is defined in the appended claims. For example, although emphasis has been placed on using a Student's t-test to draw conclusions about the cleanliness of a device, other statistical tests, known to those of ordinary skill, can be used.

What is claimed is:

1. A method for establishing the cleanliness of a device based on a test that employs an ion mobility spectrometer (IMS), the method comprising:

measuring $n_1 \geq 1$ target signal strengths with the IMS, wherein the step of measuring $n_1 \geq 1$ target signal strengths includes providing a target sample having a known concentration of a contaminant and measuring a target signal strength of the target sample with the IMS;

measuring $n_2 \geq 1$ test signal strengths of a device sample with the IMS;

obtaining a value of a statistical confidence-level parameter that is associated with a particular confidence level;

utilizing the value of a the statistical confidence-level parameter and the $n_1$ target signal strengths to obtain a pass range of signal strengths;

calculating an average test signal strength from the $n_2$ test signal strengths; and determining that the device passes the test, indicating that the device is significantly clean to within the particular confidence level, if the average test signal strength lies in the pass range.

2. The method of claim 1, wherein the step of measuring $n_1 \geq 1$ target signal strengths further comprises:

repeating the steps of providing and of measuring the target signal strength to obtain all $n_1$ target signal strengths.

3. The method of claim 1, wherein the step of measuring $n_2 \geq 1$ test signal strengths comprises:

acquiring the device sample from the device;

measuring a test signal strength of the device sample with the IMS; and repeating the steps of acquiring and of measuring the test signal strength to obtain all $n_2$ target signal strengths.

4. The method of claim 3, wherein the step of acquiring comprises:

taking a swab from the device; and extracting the swab with an appropriate amount of solvent.

5. The method of claim 3, wherein the step of measuring a test signal strength of the device sample comprises:

ionizing the device sample; and subjecting the ionized sample to ion mobility spectrometry.

6. The method of claim 1, wherein, in the step of obtaining, the statistical confidence-level parameter is a Student's t parameter.

7. The method of claim 6, wherein the step of utilizing comprises obtaining a pooled standard deviation.

8. The method of claim 7, wherein the pooled standard deviation, s, is given by $$s = \left[ \frac{\sum_{i=1}^{n_1}(x_i - \bar{x})^2 + \sum_{j=1}^{n_2}(y_j - \bar{y})^2}{n_1 + n_2 - 2} \right]^{1/2}$$

with $$\bar{x} = \frac{1}{n_1}\sum_{i=1}^{n_1} x_i$$

and $$\bar{y} = \frac{1}{n_2}\sum_{j=1}^{n_2} y_j,$$

where $\{x_1, \ldots, x_{n_1}\}$ are the $n_1$ target signal strengths and $\{y_1, \ldots, y_{n_2}\}$ are the $n_2$ test signal strengths.

9. The method of claim 8, wherein the step of utilizing further includes calculating a threshold strength, $z_t$, given by $$z_t = \bar{x} - ts\sqrt{\frac{n_1 + n_2}{n_1 n_2}},$$

the pass range being given by $[0, z_t]$.

10. The method of claim 9, further comprising determining that the device does not pass the test, indicating that the device is not significantly clean to within the particular confidence level, if the average test signal strength lies in a fail range given by the complement of the pass range, $(z_t, \infty)$.

11. The method of claim 10, wherein the fail range is divided into two ranges, a first range $(z_t, \bar{x}]$, and a second range $(\bar{x}, \infty)$, where if the average test signal strength lies in the first range the device is clean, but not significantly clean, and if the average test signal strength lies in the second range, the device is not clean.

12. A method for establishing the cleanliness of a device based on a test that employs an ion mobility spectrometer (IMS), the method comprising acquiring a device sample by taking a swab from the device;

extracting the swab with an appropriate amount of solvent;

measuring $n_2 \geq 1$ test signal strengths of the device sample with the IMS;

supplying a value of a statistical confidence-level parameter, which is associated with a particular confidence level, to determine a pass range of signal strengths; and determining that the device passes the test, indicating that the device is significantly clean to within the particular confidence level, if the $n_2$ test signal strengths yield an average test signal strength that lies in the pass range.

13. The method of claim 12, wherein the step of measuring $n_2 \geq 1$ test signal strengths comprises:

repeating the steps of acquiring the device sample and of measuring the test signal strength to obtain all $n_2$ test signal strengths.

14. The method of claim 12, wherein the appropriate amount of solvent the appropriate amount of solvent to extract the swab is given by $$V_{ex} = \frac{1}{1000} FDCA \frac{V_{ts}}{m_{ts}}$$

wherein $V_{ex}$ is a volume that the swab is extracted into, F is a recovery factor for swabbing a surface, D is a dilution factor, C is a target surface concentration, A is an area to be swabbed, $V_{ts}$ is a target sample volume to be analyzed, $m_{ts}$ is a target sample mass to be analyzed.

15. The method of claim 12, wherein the step of measuring a test signal strength of the device sample comprises:

ionizing the device sample; and subjecting the ionized sample to ion mobility spectrometry.

16. The method of claim 12, wherein, in the step of supplying, the statistical confidence-level parameter is a Student's t parameter.

17. The method of claim 16, wherein, in the step of supplying, $n_1 \geq 1$ target signal strengths from a target sample of known concentration, which are obtained with the IMS, are used to obtain the pass range.

18. The method of claim 17, wherein, in the step of supplying, the pass range is given by $[0, z_r]$, where $$z_t = \bar{x} - ts\sqrt{\frac{n_1 + n_2}{n_1 n_2}},$$

where s is a pooled standard deviation obtained from the $n_1 \geq 1$ target signal strengths and the $n_2 \geq 1$ test signal strengths, and where $\bar{x}$ is the average of the $n_1 \geq 1$ target signal strengths.

19. The method of claim 18, wherein the pooled standard deviation, s, is given by $$s = \left[ \frac{\sum_{i=1}^{n_1} (x_i - \bar{x})^2 + \sum_{j=1}^{n_2} (y_j - \bar{y})^2}{n_1 + n_2 - 2} \right]^{1/2}$$

where $\bar{y}$ is the average of the $n_2 \geq 1$ test signal strengths.

20. A system for establishing the cleanliness of a device by performing a test, the system comprising an ion mobility spectrometer (IMS) to measure $n_1 \geq 1$ target signal strengths containing a known concentration of target sample, and to measure $n_2 \geq 1$ test signal strengths of a device sample;

a statistics module to obtain a value of a statistical confidence-level parameter that is associated with a particular confidence level;

a pass range module to obtain a pass range of signal strengths from the value of the statistical confidence-level parameter and the $n_1$ target signal strengths;

an averaging module to obtain an average test signal strength from the $n_2$ test signal strengths; and a results module to determine that the device passes the test, indicating that the device is significantly clean to within the particular confidence level, if the average test signal strength lies in the pass range.

21. The system of claim 20, wherein the system is configured to measure $n_1 \geq 1$ target signal strengths by providing a target sample having a known target concentration of a contaminant for IMS analysis;

measuring a target signal strength of the target sample that is measured with the IMS; and repeating the steps of providing a target sample and of measuring the target signal strength to obtain all $n_1$ target signal strengths.

22. The system of claim 21, wherein the system is configured to measure $n_2 \geq 1$ test signal strengths of the device sample is acquired from the device by measuring a test signal strength of the device sample that is measured with the IMS; and repeating the steps of acquiring the device sample and of measuring the test signal strength to obtain all $n_2$ target signal strengths.

23. The system of claim 22, further comprising a swab for swabbing the device; and solvent for extracting the swab.

24. The system of claim 23, wherein the IMS includes an ionizer for ionizing the device sample before subjecting the ionized sample to ion mobility spectrometry.

25. The system of claim 20, wherein the statistical confidence-level parameter is a Student's t parameter.

26. The system of claim 25, wherein the pass range module includes a deviation module for calculating a pooled standard deviation to obtain the pass range.

27. The system of claim 26, wherein the pooled standard deviation, s, is given by $$s = \left[ \frac{\sum_{i=1}^{n_1}(x_i - \bar{x})^2 + \sum_{j=1}^{n_2}(y_i - \bar{y})^2}{n_1 + n_2 - 2} \right]^{1/2}$$

with $$\bar{x} = \frac{1}{n_1}\sum_{i=1}^{n_1} x_i$$

and $$\bar{y} = \frac{1}{n_2}\sum_{j=1}^{n_2} y_j,$$

where $\{x_1, \ldots, x_{n_1}\}$ are the $n_1$ target signal strengths and $\{y_1, \ldots, y_{n_2}\}$ are the $n_2$ test signal strengths.

28. The system of claim 27, wherein the pass range module further includes a threshold module for calculating a threshold strength, $z_t$, given by $$z_t = \bar{x} - ts\sqrt{\frac{n_1 + n_2}{n_1 n_2}},$$

the pass range being given by $[0, z_t]$.

29. The system of claim 28, wherein the results module determines that the device does not pass the test, indicating that the device is not significantly clean to within the particular confidence level, if the average test signal strength lies in a fail range given by the complement of the pass range, $(z_t, \infty)$.

30. The system of claim 29, wherein the fail range is divided into two ranges, a first range $(z_t, \bar{x}]$, and a second range $(\bar{x}, \infty)$, where if the average test signal strength lies in the first range the device is clean, but not significantly clean, and if the average test signal strength lies in the second range, the device is not clean.

31. The method of claim 1, further comprising determining a target mass for a known contaminant, wherein the target mass is determined by plotting a curve of average signal strength versus mass for the known contaminant and selecting a target mass that falls within the limit of the linear portion of the curve.

32. The method of claim 4, wherein the appropriate amount of solvent to extract the swab is given by $$V_{ex} = \frac{1}{1000} FDCA \frac{V_{ts}}{m_{ts}}$$

where $V_{ex}$ is a volume that the swab is extracted into, F is a recovery factor for swabbing a surface, D is a dilution factor, C is a target surface concentration, A is an area to be swabbed, $V_{ts}$ is a target sample to volume to be analyzed, $M_{ts}$ is a target sample mass to be analyzed.

33. The method of claim 12, wherein the step of determining comprises obtaining a value of a statistical confidence-level parameter that is associated with a particular confidence level; and utilizing the value of a the statistical confidence-level parameter and the $n_1$ target signal strengths to obtain a pass range of signal strengths.

* * * * *